(12) United States Patent
Hillis et al.

(10) Patent No.: US 6,809,818 B2
(45) Date of Patent: Oct. 26, 2004

(54) SATELLITE AND RETROREFLECTOR ATMOSPHERIC SPECTROSCOPY SYSTEM

(75) Inventors: W. Daniel Hillis, Encino, CA (US); Bran Ferren, Beverly Hills, CA (US)

(73) Assignee: Applied Minds, Inc., Glendale, CA (US)

( * ) Notice: Subject to any disclaimer, the term of this patent is extended or adjusted under 35 U.S.C. 154(b) by 119 days.

(21) Appl. No.: 10/327,313

(22) Filed: Dec. 20, 2002

(65) Prior Publication Data

US 2003/0142306 A1 Jul. 31, 2003

Related U.S. Application Data

(60) Provisional application No. 60/344,129, filed on Dec. 20, 2001.

(51) Int. Cl.[7] .................................................. G01J 3/42
(52) U.S. Cl. ...................................................... 356/326
(58) Field of Search ................................. 356/326, 328

(56) References Cited

U.S. PATENT DOCUMENTS 6,509,566 B1 * 1/2003 Wamsley et al. ......... 250/338.5

OTHER PUBLICATIONS

Sugimoto et al, Laser Long–Path Absorption Measurements of Atmospheric Trace Species Using The Retroreflector In Space (RIS) on the ADEOS, Geoscience and Remote Sensing Symposium 1993. IGARSS '93. 18–21 Aug. 1993, vol. 4, pp. 2141–2143.*

Aircraft Laser Infrared Absorption Spectrometer (ALIAS) (website printout).

3M Scotchlite Reflective Material (website printout).

ATMOS Atmospheric Trace Molecule Spectroscopy Experiment (website printout).

Table Mountain Facility, AVM (website printout).

* cited by examiner

*Primary Examiner*—F. L. Evans
(74) *Attorney, Agent, or Firm*—Glenn Patent Group; Michael A. Glenn

(57) ABSTRACT

A method and apparatus for obtaining atmospheric spectroscopy measurements from an observation platform using retroreflectors is disclosed. The observation platform is located above the surface of a planetary body, and at least one retroreflector is located on the surface of the planetary body. Electromagnetic radiation from a radiation source that is incident upon the retroreflector is reflected to a spectrometer located on the observation platform. By analyzing the received radiation, the spectrometer obtains atmospheric spectroscopy measurements for the atmospheric region through which the incident and reflected radiation pass.

24 Claims, 4 Drawing Sheets

SATELLITE AND RETROREFLECTOR ATMOSPHERIC SPECTROSCOPY SYSTEM

This application claims the benefit of Provisional Application No. 60/344,129, filed Dec. 20, 2001.

BACKGROUND

1. Technical Field

The invention relates to atmospheric spectroscopy systems. More particularly, the invention relates to atmospheric spectroscopy systems designed to obtain measurements in atmospheric regions above areas to which access is difficult.

2. Description of the Prior Art

Systems capable of measuring the chemical composition of the Earth's atmosphere have proven to be of great utility in a wide range of scientific research. Atmospheric spectroscopy is one commonly used technique for making such measurements. Atmospheric spectroscopy has, in part, enabled the study of increasing urban pollution, global warming, and the depletion of the ozone layer.

One difficulty faced in applying atmospheric spectroscopy is that of gaining access to the atmospheric region for which measurements are desired. One very direct approach is to transport the spectrometer to the desired location. An emitter and receiver pair, typically a laser and an optical transducer in close proximity, then take measurements for the point of interest.

An example of this technique is the Aircraft Laser Infrared Absorption Spectrometer (ALIAS) (http://laserweb.jpl.nasa.gov/alias.htm), a "high resolution four-channel scanning tunable diode laser spectrometer (3.4–8.0 $\mu$m) which makes direct, simultaneous measurements of HCl, NO2, CH4, N2O, and CO . . . in the stratosphere and troposphere at sub-parts-per-billion sensitivities."

In another approach, measurements are made for a column of air above a ground-based instrument. In this case, radiation is emitted upwards, and the reflected or backscattered radiation is analyzed. One such system is in use at the NASA Light Detection and Ranging laboratory (http://tmf-web.jpl.nasa.gov/projects.html). "The systems are designed to make high-precision, long-term measurements to aid in the detection of atmospheric changes." More specifically, "a Nd:YAG-based system is used for measurements from ground up to 15 to 20 km altitude, a combination Nd:YAG and excimer based system is used for measurements from 15 km to 55 km for ozone and 15 km to 90 km for temperature."

Finally, the NASA ATMOS observatory (http://remus.jpl.nasa.gov/atmos/) operates from orbit around the Earth, making measurements "at altitudes between 10 and 150 km". The observatory makes measurements by monitoring the absorption of solar radiation by the atmosphere during "those periods during each orbit of the spacecraft when the atmosphere is between the Sun and the instrument (i.e., at sunrise and sunset as seen from the spacecraft)".

Each of these approaches presents a set of associated difficulties. While airborne measurements do allow a single spectrometer to be used at a great number of locations, it is often impractical, if not impossible, due to political and other restrictions on airspace, to transport spectrometers to all possible regions of interest. Earth-based systems are even less versatile in that the spectrometers are typically not easily repositioned, and each unit is too costly to allow for widespread deployment of units. While the ATMOS observatory can take measurements at an expansive set of points within the atmosphere, measurements can only be made when the location of interest is in sunrise or sunset relative to the orbiting observatory. Furthermore, measurements must be made very rapidly, as "the height of the tangent point changes at about 2 kilometers per second so that, to be able to distinguish changes in the composition with altitude, successive measurements of the spectrum must be made very rapidly" (http://remus.jpl.nasa.gov/atmos/). Finally, taking measurements tangentially through the atmosphere limits the lowest elevation for which data can be obtained.

It would be advantageous to provide an atmospheric spectroscopy technique that can quickly and efficiently probe many locations within the atmosphere of the Earth. Such technique should allow for measurement of atmospheric composition above surface regions of the Earth that are not readily accessible to large and complicated surface equipment. In particular, it would be beneficial to detect the spread of chemical contamination within the atmosphere, including atmospheric regions above countries to which access is restricted. Finally, such technique should preferably be capable of operating in a passive mode, taking spectroscopic measurements using external radiation sources.

SUMMARY OF THE INVENTION

The invention is directed towards obtaining atmospheric spectroscopy measurements from an observation platform using retroreflectors. The observation platform is located above the surface of a planetary body, and at least one retroreflector is located on the surface of the planetary body. Electromagnetic radiation from a radiation source incident upon the retroreflector is reflected to a spectrometer located on the observation platform. By analyzing the received radiation, the spectrometer obtains atmospheric spectroscopy measurements for the atmospheric region through which the incident and reflected radiation pass.

In the preferred embodiment of the invention, a satellite serves as the observation platform, and is positioned at the L1 Lagrange point of the Earth-Sun system. Radiation from the Sun facilitates the spectroscopic measurements.

In an alternative, equally preferred embodiment of the invention, a satellite is positioned at the L2 Lagrange point of the Earth-Sun system. A radiation source onboard the satellite, preferably a laser, is directed toward the retroreflector.

In either geometry, the incident pathway between the radiation source and the retroreflector is essentially coincident with the reflected pathway between the retroreflector and the observation platform. In other embodiments of the invention, however, the incident and reflected pathways may be separated by a small angle, as permitted by the dispersive behavior of the retroreflector.

One or more corner mirrors, preferably an octahedral array of corner mirrors, may be used as a retroreflector. Alternatively, retroreflective materials may be used. The spectroscopic measurements may be made using radiation of various wavelengths, including visible light, infrared, microwave, radio, an x-ray. Finally, in alternative embodiments of the invention, spacecraft and aircraft serve as the observation platform.

DETAILED DESCRIPTION OF A PREFERRED AND ALTERNATIVE EMBODIMENTS

Figure 1:
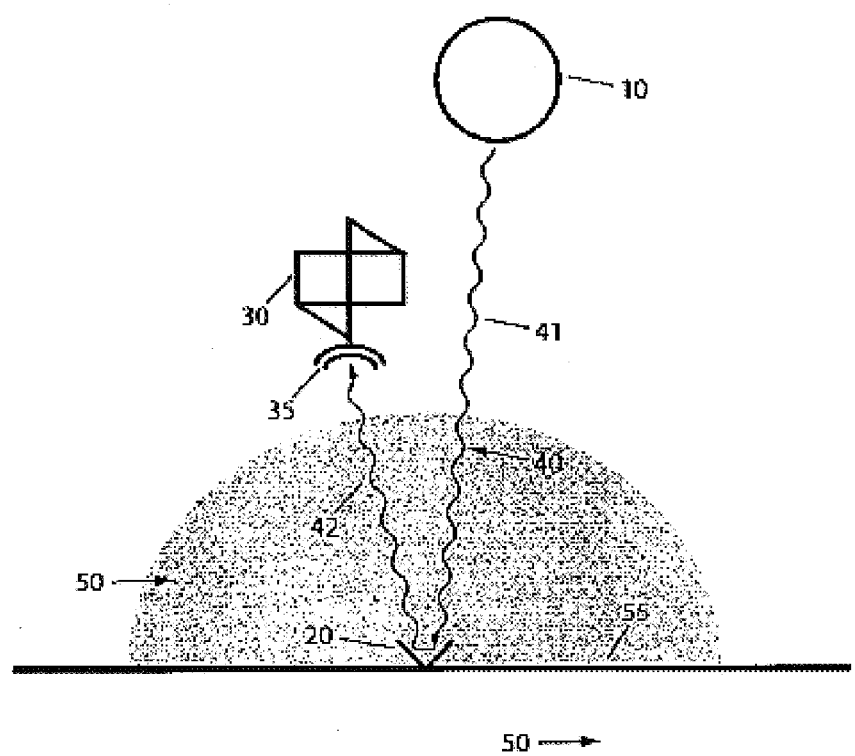
FIG. 1 is a schematic diagram that shows a retroreflector atmospheric spectroscopy system according to the invention.

FIG. 1 is a schematic diagram that shows a retroreflector atmospheric spectroscopy system according to the invention. An observation platform 30 is located above the surface 55 of a planetary body 50. A radiation source 10 emits radiation that is incident upon a retroreflector 20 located on the surface of the planetary body. The radiation travels along an incident pathway 41 from the radiation source to the retroreflector and along a reflected pathway 42 from the retroreflector to the observation platform.

Collectively, the incident pathway and the reflected pathway define a measurement pathway 40 that passes through an atmospheric region 60 in the vicinity of the retroreflector. The reflected radiation is received by a spectrometer 35 located on the observation platform. Analysis of the radiation received by the spectrometer therefore provides atmospheric spectroscopy measurements for the atmospheric region in the vicinity of the retroreflector.

A retroreflector is designed to reflect incident radiation directly back along the incident path. In practice, however, the retroreflector exhibits a degree of dispersion, characterized by an angular distribution of reflected intensity. For a specific spectroscopic measurement that requires a minimum reflected intensity, acceptable measurements may be acquired for reflected pathways that are offset from the incident pathway by less than a particular dispersion angle. Thus, while it is preferable that the incident and reflected pathway be as nearly coincident as possible, measurements may still be obtained for incident and reflected pathways that are not precisely coincident. Specifically, by defining a measurement angle as the angle between the incident and reflected pathways, measurements may be obtained if the measurement angle is less than the dispersion angle of the retroreflector.

Figure 2:
FIG. 2 is a schematic diagram that shows a satellite and retroreflector atmospheric spectroscopy system according to the invention.

FIG. 2 is a schematic diagram that shows a satellite and retroreflector atmospheric spectroscopy system according to the invention. A satellite 32 orbits the Earth 52. One or more retroreflectors 20 are located on the surface of the Earth beneath atmospheric regions of interest. The satellite is preferably positioned at the L1 Lagrange point of the Earth-Sun system. Positioning the satellite at the L1 Lagrange point ensures that the satellite remains positioned directly between the Sun and the Earth.

Figure 3:
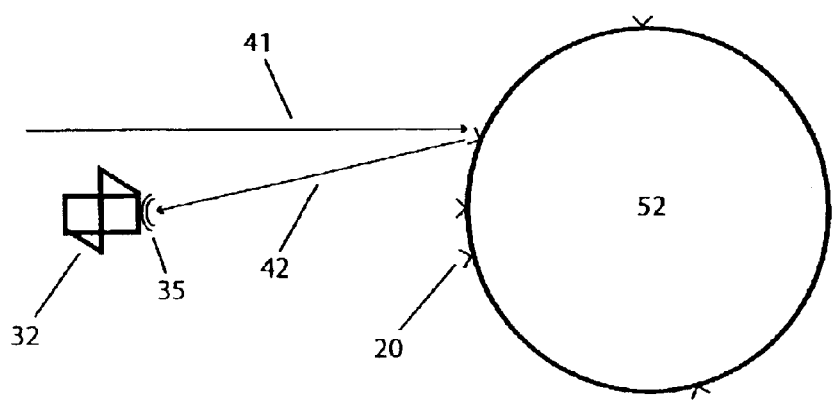
FIG. 3 is a schematic diagram that shows a detailed view of a satellite and retroreflector atmospheric spectroscopy system according to the embodiment of the invention shown in FIG. 2.

FIG. 3 is a schematic diagram that shows a detailed view of a satellite and retroreflector atmospheric spectroscopy system according to the embodiment of the invention shown in FIG. 2. Radiation from the Sun propagates along an incident pathway 41, and is reflected by a retroreflector 20 back to a spectrometer 35 on the satellite 32 along a reflected pathway 42. Because the L1 Lagrange point is approximately $1.5 \times 10^6$ km, over 100 Earth diameters, from the center of the Earth, the measurement angle formed by the incident pathway and reflected pathway is very small. In particular, the measurement angle is substantially less than the dispersion angle of a typical retroreflector.

By analyzing the absorptive properties of the atmosphere along the incident 41 and reflected 42 pathways, the chemical composition of the atmosphere along the measurement pathway can be determined. Any of the columnar absorption spectroscopy techniques known in the prior art may be used to detect a chemical species of interest. In particular, it is possible to determine the presence of chemical contaminants, such as those present after a chemical disaster or chemical warfare attack. The radiation analyzed by the spectrometer may be of various wavelengths. For example, visible light may prove especially useful, though shorter wavelength radiation such as x-rays and longer wavelength radiation such as infrared, radio, and microwave may also be analyzed.

Figure 4:
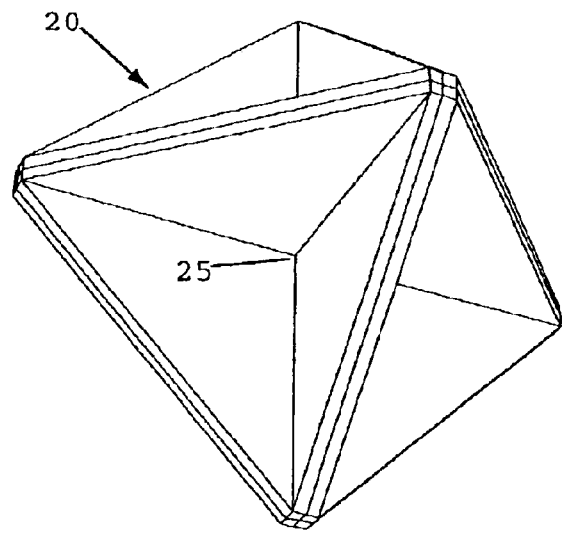
FIG. 4 is a schematic diagram that shows a retroreflector according to the invention.

FIG. 4 is a schematic diagram that shows a retroreflector according to the invention. The retroreflector 20 consists of an octahedral array of corner mirrors 25. The design ensures that at least one corner mirror is oriented to reflect incident radiation, as shown in FIG. 3. Alternative embodiments of the invention use a single corner mirror, or employ materials such as Scotchlite (TM) Retroreflective Reflectors, available from 3M (http://www.mmm.com). Such materials reflect a large fraction of the incident light directly back along the incident path for a wide range of incident angles.

Regardless of the geometry and material, the retroreflector is easier to distribute than the comparatively cumbersome and complicated ground based spectrometers. Retroreflectors such as those of FIG. 4 can be placed with relative ease in locations of restricted access, whether dropped from aircraft or positioned by ground-based researchers. Furthermore, spectroscopic measurements are not restricted to those atmospheric regions along a line between the satellite and the Sun tangent to the Earth. Rather, with an appropriately positioned retroreflector, measurements may be made for nearly any atmospheric region within view of the satellite and illuminated by the Sun. The satellite and retroreflector system allows for simple and efficient acquisition of spectroscopic measurements for a wide range of atmospheric regions.

Figure 5:
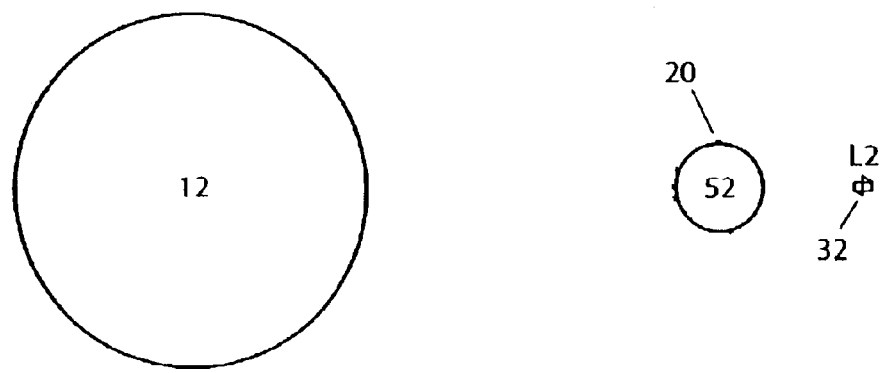
FIG. 5 is a schematic diagram that shows a satellite and retroreflector atmospheric spectroscopy system according to an alternative embodiment of the invention.

FIG. 5 is a schematic diagram that shows a satellite and retroreflector atmospheric spectroscopy system according to an alternative embodiment of the invention. A satellite 32 orbiting the Earth 52 is positioned at the L2 Lagrange point of the Earth-Sun system. Placement of the satellite at the L2 Lagrange point ensures that the satellite always remains diametrically opposite the Sun 12 with respect to the Earth. One or more retroreflectors 20 are located on the surface of the Earth beneath atmospheric regions of interest.

Figure 6:
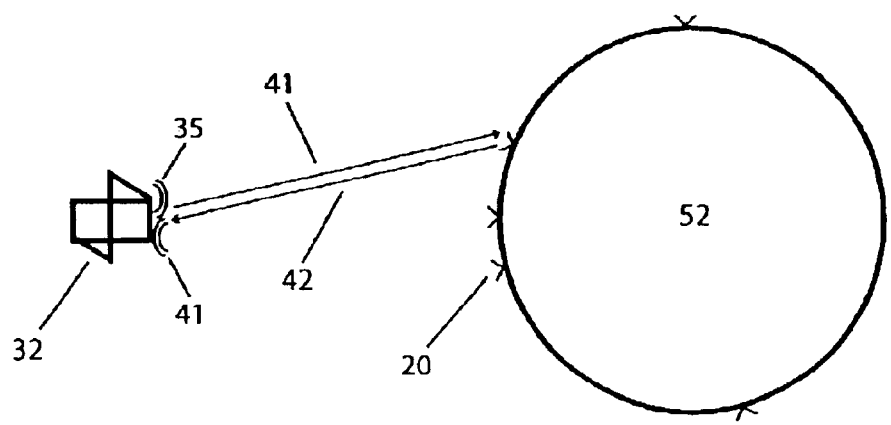
FIG. 6 is a schematic diagram that shows a detailed view of a satellite and retroreflector atmospheric spectroscopy system according to the alternative embodiment of the invention shown in FIG. 5.

FIG. 6 is a schematic diagram that shows a detailed view of a satellite and retroreflector atmospheric spectroscopy system according to the alternative embodiment of the invention shown in FIG. 5. The satellite 32 is equipped with an onboard radiation source 14. Radiation from the onboard radiation source propagates along an incident pathway 41 to a retroreflector 20. The radiation is reflected back along a reflected pathway 42 to a spectrometer 35 located on the satellite.

Because the the satellite is positioned at the L2 Lagrange point, spectroscopic measurements are made in darkness, with relatively little interference from solar radiation. A higher signal to noise ratio and therefore more precise atmospheric spectroscopy measurements may therefore be obtained. Preferably, the radiation emitted by the radiation source is lased to increase the transmission efficiency between the radiation source and the spectrometer.

Because the L1 and L2 Lagrange points are not stable equilibrium points, it may be desirable to orbit the satellite around the L1 or L2 Lagrange point. Also, difficulties may arise in communicating data from a satellite at the L1 Lagrange point back to the Earth because communication signals emitted from the satellite may be overwhelmed by radiation emitted from the Sun. It may therefore be desirable to position one or more auxiliary satellites to serve as communication relays.

Alternative embodiments of the invention may also incorporate observation platforms other than satellites. In particular, aircraft and spacecraft, including balloons, airplanes, or rockets may be used. Because such craft typically operate at altitudes lower than that of the L1 or L2 Lagrange points, the areal extent for which data may be gathered from a single craft position is reduced from that of the satellite. Depending on the dispersion angle of the retroreflector, it may be desirable to maneuver the craft to several different positions to obtain measurements for widely separated atmospheric regions.

Finally, the invention may find application in obtaining spectrometry measurements in mediums other than gaseous atmospheres. Most notably, the invention may be used to analyze the composition of oceans and other bodies of water.

Although the invention is described herein with reference to several embodiments, including the preferred embodiment, one skilled in the art will readily appreciate that other applications may be substituted for those set forth herein without departing from the spirit and scope of the invention. For example, the position of the observation platform and the retroreflectors may be reversed. That is, the observation point may be on the Earth's surface, while the retroreflectors may be placed in orbit about the Earth.

Accordingly, the invention should only be limited by the following claims.

What is claimed is:

1. An atmospheric spectroscopy system, comprising:
   an observation platform located above a surface of a planetary body;
   at least one retroreflector located on said surface;
   a radiation source for emitting electromagnetic radiation along an incident pathway towards said retroreflector, said retroreflector reflecting at least a portion of said electromagnetic radiation along a reflected pathway, said incident and said reflected pathways collectively defining a measurement pathway that passes through an atmospheric region of said planetary body; and
   a spectrometer located on said observation platform for analyzing electromagnetic radiation received at said spectrometer from said retroreflector to provide an atmospheric spectroscopy measurement for said atmospheric region.

2. The atmospheric spectroscopy system of claim 1, wherein said incident pathway and said reflected pathway are substantially coincident.

3. The atmospheric spectroscopy system of claim 1, wherein said incident pathway and said reflected pathway define a measurement angle, said measurement angle being less than a dispersion angle of said retroreflector.

4. The atmospheric spectroscopy system of claim 1, wherein said planetary body is the planet Earth.

5. The atmospheric spectroscopy system of claim 1, wherein said observation platform is any of a satellite, an aircraft, and a spacecraft.

6. The atmospheric spectroscopy system of claim 1, wherein said observation platform is a satellite that is located at any of an L1 Lagrange point and an L2 Lagrange point.

7. The atmospheric spectroscopy system of claim 1, wherein said radiation source is the Sun.

8. The atmospheric spectroscopy system of claim 1, wherein said radiation source is located on said observation platform.

9. The atmospheric spectroscopy system of claim 8, wherein said radiation source is a laser.

10. The atmospheric spectroscopy system of claim 1, wherein said retroreflector comprises at least one corner mirror.

11. The atmospheric spectroscopy system of claim 1, wherein said retroreflector comprises a retroreflective material.

12. An atmospheric spectroscopy system, comprising:
    an observation location relative to a surface of a planetary body;
    at least one retroreflector spaced from said observation location, wherein one of said observation location and said retroreflector is positioned at said planetary body surface;
    a radiation source located at said observation location for emitting electromagnetic radiation along an incident pathway towards said retroreflector, said retroreflector reflecting at least a portion of said electromagnetic radiation toward said radiation source along a reflected pathway, said incident and said reflected pathways collectively defining a measurement pathway that passes through an atmospheric region of said planetary body; and
    a spectrometer located at said observation location for analyzing radiation received at said spectrometer from said retroreflector to provide an atmospheric spectroscopy measurement for said atmospheric region.

13. An atmospheric spectroscopy method, comprising the steps of:
    locating an observation platform above a surface of a planetary body;
    locating at least one retroreflector on said surface;
    emitting electromagnetic radiation from a radiation source along an incident pathway towards said retroreflector, said retroreflector reflecting at least a portion of said electromagnetic radiation toward said radiation source along a reflected pathway, said incident and said reflected pathways collectively defining a measurement pathway that passes through an atmospheric region of said planetary body; and
    locating a spectrometer on said observation platform for analyzing electromagnetic radiation received at said spectrometer from said retroreflector to provide an atmospheric spectroscopy measurement for said atmospheric region.

14. The atmospheric spectroscopy method of claim 13, wherein said incident pathway and said reflected pathway are substantially coincident.

15. The atmospheric spectroscopy method of claim 13, wherein said incident pathway and said reflected pathway define a measurement angle, said measurement angle being less than a dispersion angle of said retroreflector.

16. The atmospheric spectroscopy method of claim 13, wherein said planetary body is the planet Earth.

17. The atmospheric spectroscopy method of claim 13, wherein said observation platform is any of a satellite, an aircraft, and a spacecraft.

18. The atmospheric spectroscopy method of claim 13, wherein said observation platform is a satellite that is located at any of an L1 Lagrange point and an L2 Lagrange point.

19. The atmospheric spectroscopy method of claim 13, wherein said radiation source is the Sun.

20. The atmospheric spectroscopy method of claim 13, wherein said radiation source is located on said observation platform.

21. The atmospheric spectroscopy method of claim 20, wherein said radiation source is a laser.

22. The atmospheric spectroscopy method of claim 13, wherein said retroreflector comprises at least one corner mirror.

23. The atmospheric spectroscopy method of claim 13, wherein said retroreflector comprises a retroreflective material.

24. An atmospheric spectroscopy method, comprising the steps of:

provide an observation location relative to a surface of a planetary body;

providing at least one retroreflector spaced from said observation location, wherein one of said observation location and said retroreflector is positioned at said planetary body surface;

locating a radiation source at said observation location for emitting electromagnetic radiation along an incident pathway towards said retroreflector, said retroreflector reflecting at least a portion of said electromagnetic radiation toward said radiation source along a reflected pathway, said incident and said reflected pathways collectively defining a measurement pathway that passes through an atmospheric region of said planetary body; and locating a spectrometer at said observation location for analyzing radiation received at said spectrometer from said retroreflector to provide an atmospheric spectroscopy measurement for said atmospheric region.

* * * * *